United States Patent
Kim et al.

(10) Patent No.: US 10,886,563 B2
(45) Date of Patent: Jan. 5, 2021

(54) POLYMER SOLID ELECTROLYTE AND LITHIUM SECONDARY BATTERY COMPRISING SAME

(71) Applicant: LG CHEM, LTD., Seoul (KR)

(72) Inventors: Seungha Kim, Daejeon (KR); Youngcheol Choi, Daejeon (KR); Jonghyun Chae, Daejeon (KR); Kyoung Hoon Kim, Daejeon (KR); Yeonju Lee, Daejeon (KR); Daeil Kim, Daejeon (KR); Lucia Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 41 days.

(21) Appl. No.: 16/330,795

(22) PCT Filed: Apr. 13, 2018

(86) PCT No.: PCT/KR2018/004316
§ 371 (c)(1),
(2) Date: Mar. 6, 2019

(87) PCT Pub. No.: WO2018/190665
PCT Pub. Date: Oct. 18, 2018

(65) Prior Publication Data
US 2019/0280332 A1    Sep. 12, 2019

(30) Foreign Application Priority Data

Apr. 14, 2017  (KR) .................. 10-2017-0048292
Apr. 12, 2018  (KR) .................. 10-2018-0042604

(51) Int. Cl.
*H01M 10/0565* (2010.01)
*H01M 10/052* (2010.01)
(Continued)

(52) U.S. Cl.
CPC ....... *H01M 10/0565* (2013.01); *C07C 309/63* (2013.01); *C07C 309/65* (2013.01);
(Continued)

(58) Field of Classification Search
None
See application file for complete search history.

(56) References Cited

U.S. PATENT DOCUMENTS

2005/0074675 A1* 4/2005 Nishijima ........... H01M 10/052
                                                      429/317
2011/0111289 A1  5/2011 Choi et al.
(Continued)

FOREIGN PATENT DOCUMENTS

JP    2002-33129 A    1/2002
JP    2002-319434 A   10/2002
(Continued)

OTHER PUBLICATIONS

Mosallanejad, "Phthalimide Derivatives: New Promising Additives for Functional Electrolyte in Lithium-ion Batteries" Chemical Methodologies 3 (2019) 261-275 (Year: 2019).*

(Continued)

*Primary Examiner* — Amanda J Barrow
(74) *Attorney, Agent, or Firm* — Birch, Stewart, Kolasch & Birch, LLP

(57) ABSTRACT

A polymer solid electrolyte having high ion conductivity and interfacial stability is provided. An additive including an organic compound having a highest occupied molecular orbital (HOMO) energy of −8.5 eV or higher is used, which facilitates film formation in a positive electrode due to low oxidation potential. The resulting polymer solid electrolytes have enhanced film formation on the surface of a positive electrode surface and enhanced interfacial stability, while (Continued)

maintaining battery performance. Lithium secondary battery having enhanced performance are also described.

8 Claims, 7 Drawing Sheets

(51) Int. Cl.

| | | |
|---|---|---|
| H01M 10/42 | (2006.01) | |
| C07C 309/65 | (2006.01) | |
| C07C 309/63 | (2006.01) | |
| C07D 333/36 | (2006.01) | |
| C07D 333/48 | (2006.01) | |
| H01M 10/0525 | (2010.01) | |
| H01M 10/0567 | (2010.01) | |
| H01M 10/0569 | (2010.01) | |
| H01M 10/0568 | (2010.01) | |

(52) U.S. Cl.
CPC ......... *C07D 333/36* (2013.01); *C07D 333/48* (2013.01); *H01M 10/052* (2013.01); *H01M 10/0525* (2013.01); *H01M 10/0567* (2013.01); *H01M 10/0568* (2013.01); *H01M 10/0569* (2013.01); *H01M 10/4235* (2013.01); *H01M 2300/0082* (2013.01); *H01M 2300/0085* (2013.01); *H01M 2300/0091* (2013.01)

(56) References Cited

U.S. PATENT DOCUMENTS

| | | | |
|---|---|---|---|
| 2013/0224535 A1 | 8/2013 | Matsuoka et al. | |
| 2014/0093783 A1 | 4/2014 | Lamanna et al. | |
| 2014/0287325 A1* | 9/2014 | Abe .................. | H01M 4/583 429/332 |
| 2015/0155559 A1 | 6/2015 | Zimmerman et al. | |
| 2017/0294682 A1* | 10/2017 | Ahn .................. | C07C 265/12 |
| 2019/0006703 A1* | 1/2019 | Ahn .................. | H01M 10/0568 |
| 2019/0036155 A1* | 1/2019 | Ahn .................. | C07C 265/02 |

FOREIGN PATENT DOCUMENTS

| | | | | |
|---|---|---|---|---|
| JP | 2004-227967 A | 8/2004 | | |
| JP | 2006-73513 A | 3/2006 | | |
| JP | 2014-146558 | * 8/2014 | .......... | H01M 10/052 |
| KR | 10-2010-0028928 A | 3/2010 | | |
| KR | 10-2011-0051618 A | 5/2011 | | |
| KR | 10-1346414 B1 | 1/2014 | | |
| KR | 10-2014-0039254 A | 4/2014 | | |
| KR | 10-1462110 B1 | 11/2014 | | |
| KR | 10-2017-0032713 A | 3/2017 | | |
| KR | 10-2017-0100682 A | 9/2017 | | |

OTHER PUBLICATIONS

European Search Report for Appl. No. 18783779.4 dated Jul. 8, 2019.
Nie, M., et al, "Development of Pyridine-Boron Trifluoride Electrolyte Additives for Lithium-Ion Batteries," Journal of Electrochemical Society, Mar. 31, 2015, vol. 162, No. 7, pp. A1186-A1195.
International Search Report (PCT/ISA/201) issued in PCT/KR2018/004316, dated Aug. 1, 2018.
Jorgensen et al., "Development and Testing of the OPLS All-Atom Force Field on Conformational Energetics and Properties of Organic Liquids", Journal of the American Chemical Society, 1996, vol. 118, No. 45, pp. 11225-11236.
Long et al., "Polymer electrolytes for lithium polmer batteries", Journal of Materials Chemistry A, 2016, vol. 4, pp. 10038-10069.
Ouatani et al., "The Effect of Vinylene Carbonate Additive on Surface Film Formation on Both Electrodes in Li-Ion Batteries", Journal of The Electrochemical Society, 2009, vol. 156, No. 2, pp. A103-A113.
Vatamanu et al., "Molecular Dynamics Simulation Studies of the Structure of a Mixed Carbonate/$LiPF_6$ Electrolyte near Graphite Surface as a Function of Electrode Potential", J. Phys. Chem. C 2012, vol. 116, pp. 1114-1121.
Wang et al., "Development and Testing of a General Amber Force Field", Journal of Computational Chemistry, vol. 25, No. 9, pp. 1157-1174.

* cited by examiner

【Figure 1】
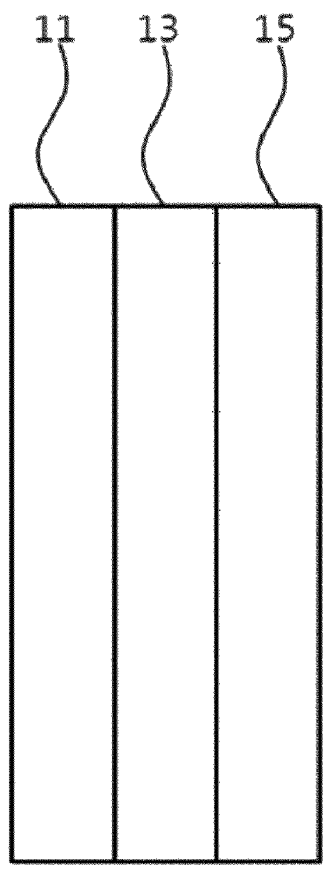

【Figure 2a】
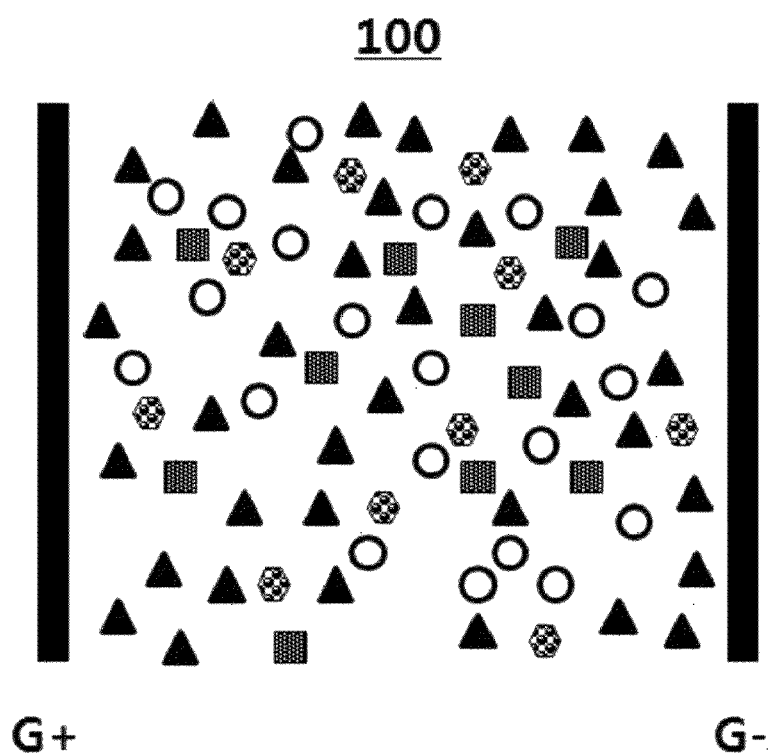

[Figure 2b]
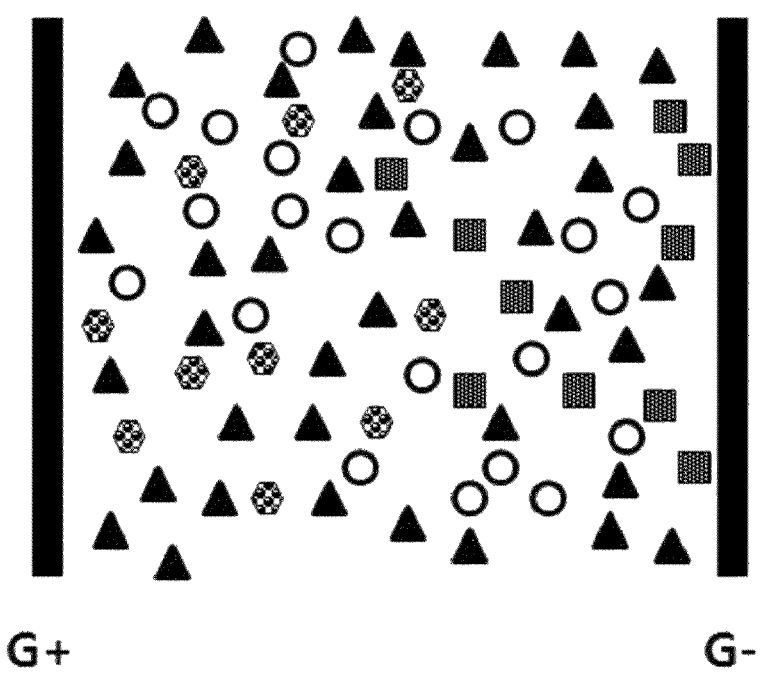

[Figure 2c]
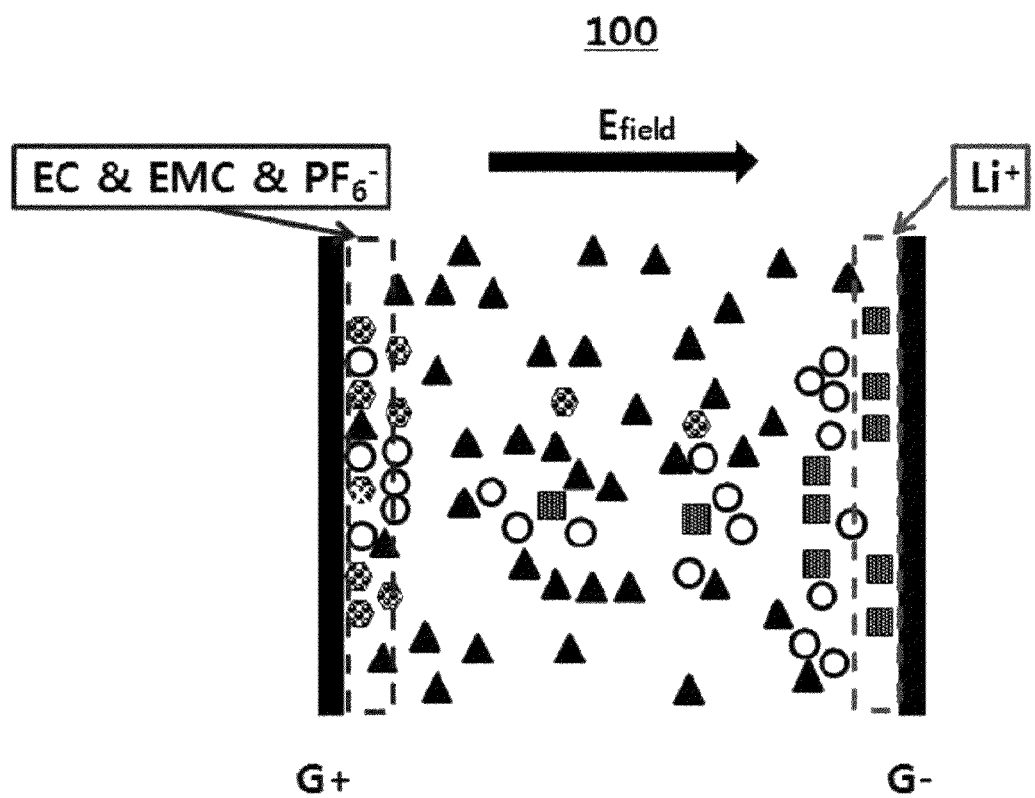

【Figure 3】
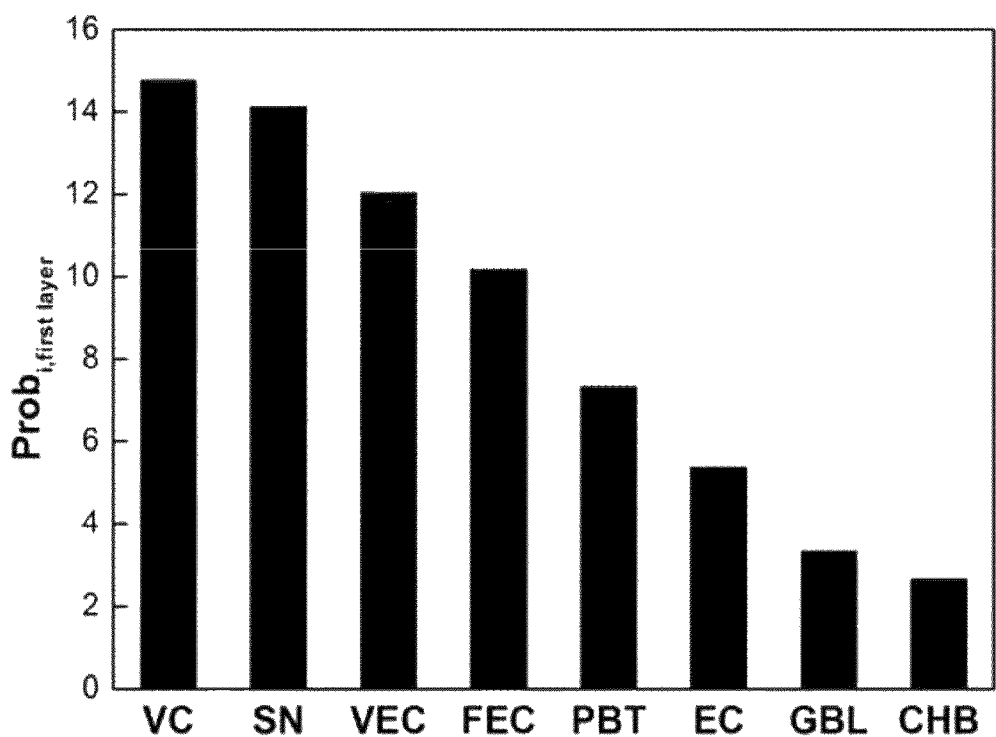

【Figure 4】
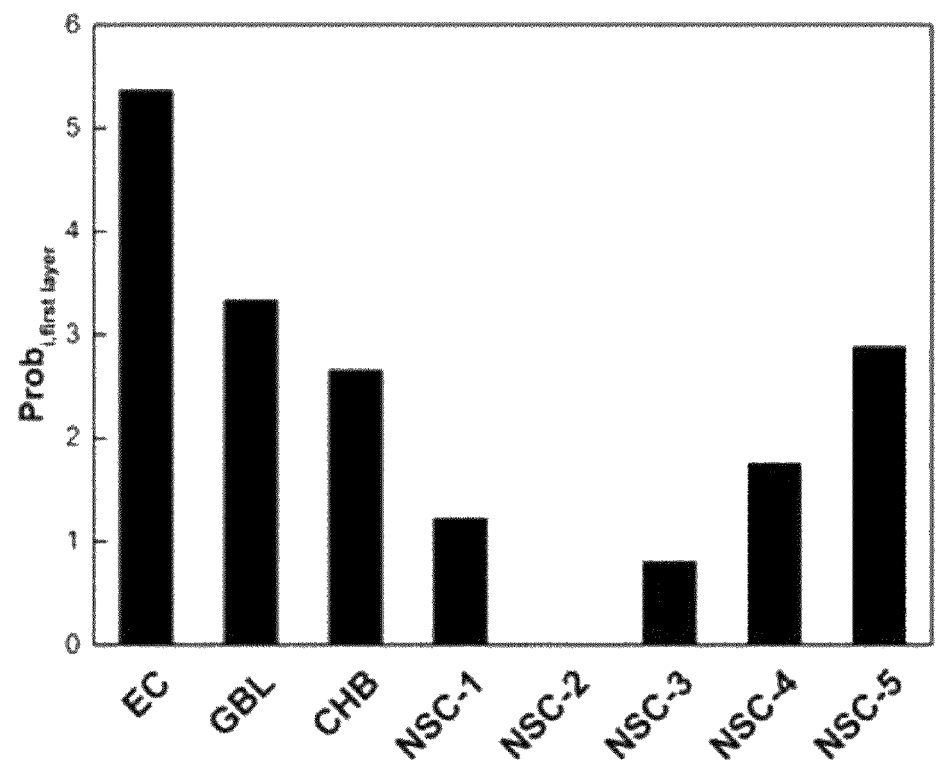

【Figure 5】
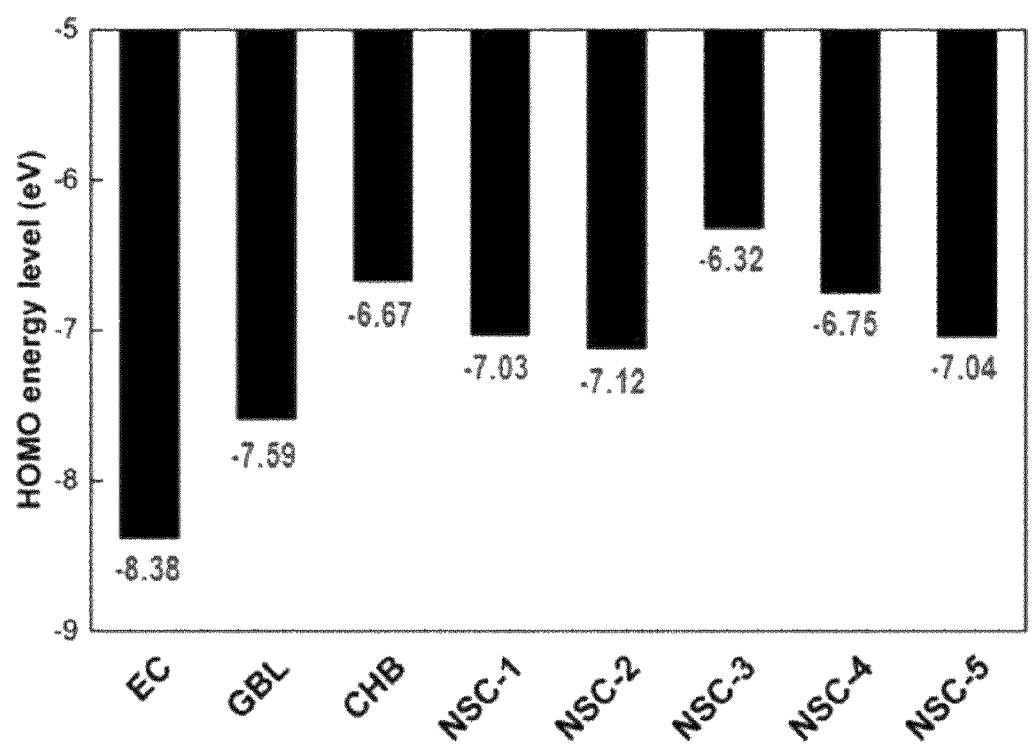

US 10,886,563 B2

POLYMER SOLID ELECTROLYTE AND LITHIUM SECONDARY BATTERY COMPRISING SAME

TECHNICAL FIELD

This application claims priority to and the benefits of Korean Patent Application No. 10-2017-0048292, filed with the Korean Intellectual Property Office on Apr. 14, 2017, and Korean Patent Application No. 10-2018-0042604, filed with the Korean Intellectual Property Office on Apr. 12, 2018, the entire contents of which are incorporated herein by reference.

The present invention relates to a polymer solid electrolyte and a lithium secondary battery comprising the same.

BACKGROUND ART

Lithium secondary batteries have been used in various industries from small electronic devices (including smart phones, laptops or tablet PCs) to car batteries and the like. Progress has been made in this technology for these to become smaller and lighter, and to have high performance and high capacity.

A lithium secondary battery includes a negative electrode, a positive electrode and an electrolyte. Lithium, carbon and the like are used as the negative electrode active material of the lithium secondary battery, and transition metal oxides, metal chalcogen compounds, conductive polymers and the like are used as the positive electrode active material, and as the electrolyte, liquid electrolytes, solid electrolytes, polymer electrolytes and the like are used.

Among these, polymer electrolytes are environmentally-friendly, without problems such as liquid leakage occurring in liquid electrolytes. They are able to be processed to a thin film and a film form, leading to an advantage of being readily modified to a desired device structure and desired forms.

A polymer electrolyte is a material formed with a polymer, a lithium salt, a non-aqueous organic solvent (optional) and other additives, and exhibits ion conductivity of approximately 10-8 S/cm, and therefore, has a problem in that performance significantly declines compared to non-aqueous liquid electrolytes.

With the purpose of overcoming such a problem in view of the above, it has been reported that ion conductivity of a polymer electrolyte may be enhanced up to 10-3 S/cm, that is similar to ion conductivity of a non-aqueous liquid electrolyte by developing an ion conducting polymer electrolyte having high ion conductivity at room temperature and thereby facilitating charge transfer between the polymer and dopants.

In such an ion conducting polymer electrolyte having high ion conductivity at room temperature, charge transfer with dopants is facilitated enhancing ion conductivity, however, unstable oxidation potential is caused leading to a problem of declining interfacial stability.

Accordingly, development of a polymer electrolyte capable of securing interfacial stability as well as excellent ion conductivity has been required.

PRIOR ART DOCUMENTS

Non-Patent Documents (1) Long et al, J. Mater. Chem. A, 2016, 10038
(2) Vatamanu et al, JPCC, 2012, 1114

DISCLOSURE

Technical Problem

In view of the above, the inventors of the present invention have conducted extensive studies for developing a polymer solid electrolyte capable of securing ion conductivity and excellent interfacial stability at the same time. As a result, the inventors have selected an organic compound having a specific highest occupied molecular orbital (HOMO) energy value as an additive. The inventors have identified that, when the organic compound has a high HOMO energy, electrons favorably escape from an electrolyte molecule leading to excellent ion conductivity. Also, oxidation is facilitated on a positive electrode surface, which is advantageous in forming a film for protecting a positive electrode. Oxidation stability at a positive electrode interface may be enhanced by adsorbing on the positive electrode surface and protecting the positive electrode surface.

Accordingly, an aspect of the present invention provides a polymer solid electrolyte for preparing a polymer solid electrolyte.

Another aspect of the present invention provides a lithium secondary battery comprising the polymer solid electrolyte.

Technical Solution

According to an aspect of the present invention, there is provided a polymer solid electrolyte comprising a polymer for an electrolyte, a lithium salt and an additive, wherein the additive is an organic compound having a highest occupied molecular orbital (HOMO) energy of −8.5 eV or higher.

The HOMO energy may be −7.6 eV or higher.

The organic compound may be one or more types selected from the group consisting of vinylene carbonate (VC); fluoroethylene carbonate (FEC); vinyl ethylene carbonate (VEC); pyridine-boron trifluoride (PBT); succinonitrile (SN); a compound represented by the following Chemical Formula 1; a compound represented by the following Chemical Formula 2; a compound represented by the following Chemical Formula 3; a compound represented by the following Chemical Formula 4; and a compound represented by the following Chemical Formula 5:

<Chemical Formula 1>

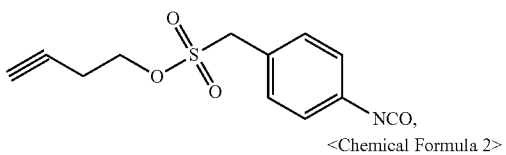

<Chemical Formula 2>

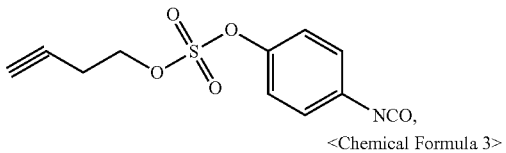

<Chemical Formula 3>

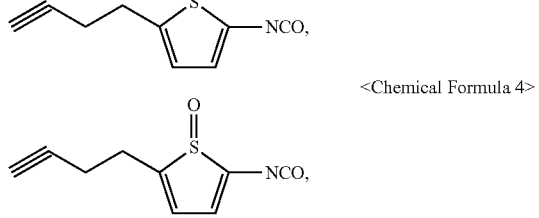

<Chemical Formula 4>

<Chemical Formula 5>

[Chemical structure: a thiophene ring with SO₂ group, connected to NCO group, and a butynyl chain]

The polymer for an electrolyte may be one or more types selected from the group consisting of polyethylene oxide (PEO), polyethylene carbonate (PEC), polypropylene carbonate (PPC), poly(vinylidene fluoride) (PVDF), poly(ethylene glycol) (PEG), polyphenylene sulfide (PPS) and derivatives thereof.

The lithium salt may be one or more types selected from the group consisting of LiCl, LiBr, LiI, LiClO$_4$, LiBF$_4$, LiB$_{10}$Cl$_{10}$, LiPF$_6$, LiAsF$_6$, LiSbF$_6$, LiAlCl$_4$, LiSCN, Li(FSO$_2$)$_2$N, LiCF$_3$CO$_2$, LiCH$_3$SO$_3$, LiCF$_3$SO$_3$, LiN(SO$_2$CF$_3$)$_2$, LiTFSI, LiFSI, LiOH, LiOH·H$_2$O, LiBOB, LiN(SO$_2$C$_2$F$_5$)$_2$, LiC$_4$F$_9$SO$_3$, LiC(CF$_3$SO$_2$)$_3$, (CF$_3$SO$_2$)$_2$NLi, LiOH.H$_2$O, LiB(C$_2$O$_4$)$_2$, chloroborane lithium, lower aliphatic carboxylic acid lithium, lithium tetraphenylborate and lithium imide.

The lithium salt may be included in an amount of 10% by weight to 30% by weight based on a total weight of the polymer solid electrolyte.

The polymer solid electrolyte may further include an organic solvent, and the organic solvent may be one or more types selected from the group consisting of 4-acetylmorpholine, 2-methylpyridine-1-oxide, 2-pyrrolidone, 1-(2-hydroxyethyl)-2-pyrrolidone, propylene carbonate (PC), ethylene carbonate (EC), 2-oxepanone, butanone, 2-pentanone and methyl ethyl ketone (MEK).

According to another aspect of the present invention, there is provided a lithium secondary battery including the polymer solid electrolyte.

Advantageous Effects

A polymer solid electrolyte according to the present invention is capable of enhancing performance of a lithium secondary battery by securing high ion conductivity, and interfacial stability in a positive electrode.

DESCRIPTION OF DRAWINGS

FIG. 1 is a sectional view illustrating a lithium secondary battery according to the present invention.

FIGS. 2a to 2c are mimetic diagrams of a cell manufactured for evaluating a degree of electrolyte components reaching a positive electrode surface using molecular dynamics.

FIG. 3 is graph showing the degree of positive electrode surface distribution (Prob$_{i, first\ layer}$) for the additives used in each polymer solid electrolyte prepared in Examples 1 to 5. Ethylene carbonate (EC), gamma-butyrolactone (GBL) and cyclohexylbenzene (CHB) were measured as a reference. The additives can be used for protecting an electrode, when charging a lithium secondary battery.

FIG. 4 is graph showing the degree of distribution (Probi, first layer) for the additives used in each polymer solid electrolyte prepared in Examples 5 to 10. Ethylene carbonate (EC), gamma-butyrolactone (GBL) and cyclohexylbenzene (CHB) were measured as a reference. The additives can be used for protecting an electrode, when included in a positive electrode surface film when charging a lithium secondary battery.

FIG. 5 is a result of measuring a HOMO energy level for an additive used in preparing each polymer solid electrolyte in Examples 6 to 10.

BEST MODE

The present invention provides a technology for preparing a polymer solid electrolyte including an additive having excellent properties in reaching a positive electrode during a charging process of a lithium secondary battery, and having excellent properties of film formation and adsorption on the positive electrode surface, and then using this in a lithium secondary battery.

Polymer Solid Electrolyte

The polymer solid electrolyte according to the present invention comprises a polymer for an electrolyte, a lithium salt and an additive, and the additive may be an organic compound having low oxidation potential with excellent properties in reaching a positive electrode, and in addition thereto, with excellent film formation and adsorption properties on the positive electrode surface due to the low oxidation potential.

The additive may be an additive for protecting an electrode, and oxidation potential of the organic compound may be defined by a highest occupied molecular orbital (HOMO) energy level. In other words, the HOMO energy level and the oxidation potential may be inversely proportional.

The HOMO energy level capable of defining the oxidation potential of the organic compound may be analyzed with a B3PW91/6-31+G* level in a Gaussian 09 program.

In the polymer solid electrolyte of the present invention, the additive may be an organic compound having HOMO energy of −8.5 eV or higher, preferably −7.6 eV or higher and more preferably −7.6 eV to −6.3 eV. When the HOMO energy of the additive is less than the above-mentioned range, a film is not readily formed on the positive electrode surface and an effect of enhancing interfacial stability may be insignificant. In addition, although an effect of enhancing interfacial stability may be superior as the HOMO energy increases, a thickness of the formed film increases when the HOMO energy is excessively high such as higher than −6.3 eV, which declines battery performance.

In addition, based on a phenomenon of electrolyte components such as an anion of a lithium salt, an electrolytic solution and an additive included in the electrolyte distributing on the positive electrode surface when charging a lithium secondary battery as a result of evaluating properties reaching the positive electrode using molecular dynamics, a degree of distribution of the electrolyte components such as an anion of a lithium salt, an electrolytic solution and an additive on the positive electrode surface during charge may be calculated, and a degree of these materials favorably reaching the positive electrode surface may be analyzed.

The organic compound may be one or more types selected from the group consisting of vinylene carbonate (VC); fluoroethylene carbonate (FEC); vinyl ethylene carbonate (VEC); pyridine-boron trifluoride (PBT); succinonitrile (SN); compounds represented by the following Chemical Formula 1; compounds represented by the following Chemical Formula 2; compounds represented by the following Chemical Formula 3; compounds represented by the following Chemical Formula 4; and compounds represented by the following Chemical Formula 5:

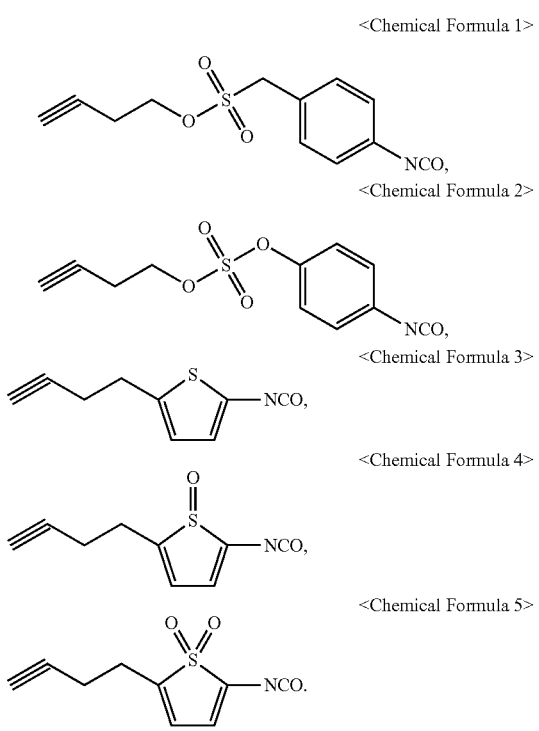

<Chemical Formula 1>
<Chemical Formula 2>
<Chemical Formula 3>
<Chemical Formula 4>
<Chemical Formula 5>

Among the organic compounds, vinylene carbonate (VC), fluoroethylene carbonate (FEC), vinyl ethylene carbonate (VEC), pyridine-boron trifluoride (PBT) and succinonitrile (SN) have also been used in existing non-aqueous liquid electrolytes, and may be represented by the following Chemical Formula 6.

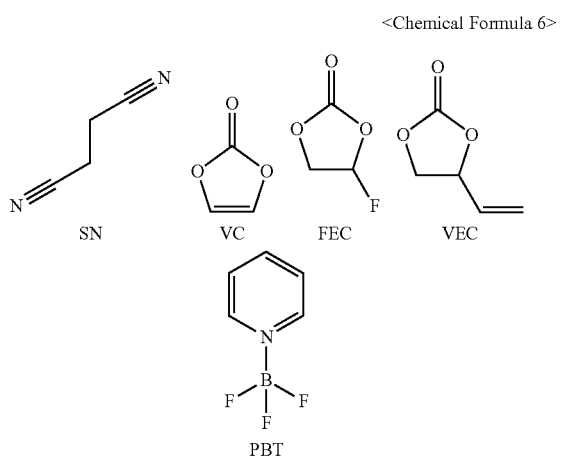

<Chemical Formula 6>

Among the organic compounds, the SN, the VC, the FEC, the VEC and the PBT represented by Chemical Formula 6 may have HOMO energy of −8.5 eV or higher and preferably −8.5 eV to −7.3 eV, and the HOMO energy of the organic compounds represented by Chemical Formula 1 to Chemical Formula 5 may be −7.6 eV or higher and preferably from −7.6 eV to −6.3 eV.

The organic compound content may be from 0.1% by weight to 20% by weight, preferably from 5% by weight to 15% by weight and more preferably from 8% by weight to 13% by weight based on a total weight of the polymer solid electrolyte. When the content is less than the above-mentioned range, a film is difficult to form in the positive electrode lowering stability at the positive electrode interface, and when the content is greater than the above-mentioned range, ion conductivity may decrease.

The polymer for an electrolyte in the polymer solid electrolyte of the present invention may be one or more types selected from the group consisting of polyethylene oxide (PEO), polyethylene carbonate (PEC), polypropylene carbonate (PPC), poly(vinylidene fluoride) (PVDF), poly(ethylene glycol) (PEG), polyphenylene sulfide (PPS) and derivatives thereof. Preferably, the polymer for an electrolyte may be poly(ethylene oxide) (PEO).

The content of the polymer for an electrolyte may be from 10% by weight to 30% by weight, preferably from 15% by weight to 25% by weight and more preferably from 18% by weight to 23% by weight based on a total weight of the polymer solid electrolyte. When the content is less than the above-mentioned range, battery lifetime may decrease, and when the content is greater than the above-mentioned range, ion conductivity may decrease.

In the polymer solid electrolyte of the present invention, a lithium salt used as an ion supplying compound may enhance lithium ion conductivity, and according to one embodiment of the present invention, the ion supplying compound may be a lithium salt.

As the lithium salt, for example, one type of lithium salt selected from the group consisting of LiCl, LiBr, LiI, $LiClO_4$, $LiBF_4$, $LiB_{10}Cl_{10}$, $LiPF_6$, $LiAsF_6$, $LiSbF_6$, $LiAlCl_4$, LiSCN, $Li(FSO_2)_2N$ $LiCF_3CO_2$, $LiCH_3SO_3$, $LiCF_3SO_3$, $LiN(SO_2CF_3)_2$, LiTFSI, LiFSI, LiOH, $LiOH·H_2O$, LiBOB, $LiN(SO_2C_2F_5)_2$, $LiC_4F_9SO_3$, $LiC(CF_3SO_2)_3$ $(CF_3SO_2)_2NLi$, $LiOH·H_2O$, $LiB(C_2O_4)_2$, chloroborane lithium, lower aliphatic carboxylic acid lithium, lithium tetraphenylborate, lithium imide and combinations thereof, and the like, may be used.

Preferably, the lithium salt is favorably included in 10% by weight to 30% by weight, preferably in 15% by weight to 25% by weight and more preferably in 17% by weight to 23% by weight in the whole polymer solid electrolyte. When the lithium salt content is less than the above-mentioned range, lithium ion conductivity is not readily secured. On the contrary, the content being greater than the above-mentioned range is uneconomical since a significant increase is not obtained in the effect, and therefore, the content is properly selected in the above-mentioned range.

As an organic solvent used for preparing the polymer solid electrolyte of the present invention, solvents capable of dissolving ion conducting compounds may be used, and as one example, the organic solvent may be one or more types selected from among polar protic solvents and hydrogen-bond (H-bond) acceptor solvents. The polar protic solvent may be selected from the group consisting of 4-acetylmorpholine, 2-methylpyridine-1-oxide, 2-pyrrolidone and 1-(2-hydroxyethyl)-2-pyrrolidone, and the H-bond acceptor solvent may be one or more types selected from the group consisting of propylene carbonate (PC), ethylene carbonate (EC), 2-oxepanone, butanone, 2-pentanone and methyl ethyl ketone (MEK).

As for the solvent content, the content is limited considering viscosity of a finally obtained polymer solid electrolyte. In other words, viscosity of a finally obtained composition is high as the solvent content increases making a preparation process of the polymer solid electrolyte membrane difficult, and as the content decreases on the contrary, viscosity is low also declining workability.

In addition, although solution viscosity of the polymer solid electrolyte of the present invention at 30° C. is not particularly limited, the viscosity may be preferably from 200 cP to 1,000 cP, preferably 300 cP to 800 cP or less and more preferably from 500 cP to 700 cP. Such viscosity control enables to secure viscosity enhancing film processability in preparing the polymer solid electrolyte to a membrane.

When the viscosity is greater than the above-mentioned range, a transverse direction (TD) thickness becomes non-uniform due to decline in the coating solution flatness, and fluidity disappears making uniform coating difficult in some cases, and when the viscosity is less than the above-mentioned range on the contrary, stain occurrences caused by an excessive flow of the coating solution may be prevented when coating, and causes a problem of mechanical direction (MD) thickness being non-uniform.

Polymer Solid Electrolyte Membrane

The polymer solid electrolyte is formed to a polymer solid electrolyte membrane by performing a known film preparation method.

Examples of the film molding method may comprise any proper film molding method such as a solution casting method, a melt extrusion method, a calendar method or a compression molding method. Among these film molding methods, a solution casting method or a melt extrusion method is preferred.

As one example, a solution casting method may be used for preparing the film.

In the solution casting method, the polymer solid electrolyte is coated. Herein, the polymer solid electrolyte may be directly coated on any one of a positive electrode or a negative electrode, or coated on a separate substrate, separating the same, and then laminated with a positive electrode and a negative electrode.

Herein, the substrate may be a glass substrate or a plastic substrate. As the plastic substrate, various plastic films such as polyethylene terephthalate, polyethylene naphthalate, polypropylene, polyethylene, cellulose triacetate, cellulose diacetate, poly(meth)acrylic acid alkyl ester, a poly(meth) acrylic acid ester copolymer, polyvinyl chloride, polyvinyl alcohol, polycarbonate, polystyrene, cellophane, a polyvinylidene chloride copolymer, polyamide, polyimide, a vinyl chloride/vinyl acetate copolymer, polytetrafluoroethylene, and polytrifluoroethylene may be included. In addition, composite materials formed with two or more types thereof may also be used, and a polyethylene terephthalate film having excellent light transmittance is particularly preferred. The support has a thickness of preferably 5 μm to 150 μm and more preferably 10 μm to 50 μm.

As examples of the coating, methods of spin coating, dip coating, solvent casting, slot die coating, spray coating, roll coating, extrusion coating, curtain coating, die coating, wire bar coating, knife coating or the like may be used.

Herein, parameter adjustments are required in each process for preparing a uniform film.

As one example, spin coating may be performed at 500 rpm to 4000 rpm or the coating process may be divided into two steps, and doctor blade coating may use a device having a thickness gap of 10 μm to 200 μm. In addition, spray coating may be performed by spraying for 5 times to 100 times of injections through an injection pressure of 0.5 MPa to 20 MPa. Such process design and parameter selection may be controlled by those skilled in the art.

After the coating, film drying may be additionally carried out.

Herein, the drying may vary depending on each constituent, the organic solvent type and the content ratio, but is preferably carried out for 30 seconds to 15 minutes at 60° C. to 100° C.

The drying may be carried out using one method among hot air drying, electromagnetic wave drying, vacuum drying, spray drying, drum drying and freeze drying, and preferably, hot air drying is used.

After carrying out the coating and the drying, the polymer solid electrolyte membrane thickness is formed to a thickness of a membrane to finally prepare, and when necessary, the coating-drying or the coating is carried out one or more times.

As another example, a melt extrusion method may be used for preparing the film.

Examples of the melt extrusion method may comprise a T die method, an inflation method and the like. The molding temperature is preferably from 150° C. to 350° C. and more preferably from 200° C. to 300° C.

When molding the film using the T-die method, a T-die is installed on the fore-end of a known monoaxial extruder or a biaxial extruder, and a roll-shaped film may be obtained by winding the film extruded in a film shape.

As necessary, the heat melting may go through processes of first heat melting, filtering filter passing and second heat melting in consecutive order. The heat melted temperature during the melt extrusion may be from 170° C. to 320° C. and preferably from 200° C. to 300° C. After melt extruded from the T die, at least one or more metal drums maintaining at 70° C. to 140° C. may be used for cooling and solidifying. When using a drum (casting roll) as above, extrusion may be carried out under the above-described temperature condition or at a lower temperature.

Specific preparation methods for preparing the polymer solid electrolyte membrane may be properly selected by those skilled in the art.

Lithium Secondary Battery

The polymer solid electrolyte provided above may be used in a lithium secondary battery due to properties such as interfacial stability on a positive electrode surface as well as high lithium ion conductivity.

Particularly, the polymer solid electrolyte of the present invention has a form of an organic compound having low oxidation potential and readily reaching a positive electrode being dispersed in a cured ion conducting compound, and by the organic compound having low oxidation potential and readily reaching a positive electrode, film formation and adsorption are facilitated in an electrode, particularly, on a positive electrode surface during charge, and as a result, enhanced interfacial stability is obtained as well as excellent properties compared to existing polymers such as polyethylene oxide or polypropylene oxide.

In addition, problems that occur when operating a lithium secondary battery (heating, explosion, film degradation and the like) are resolved due to heat resistance, durability, chemical resistance, flame retardancy and the like, and voltage stability of the lithium secondary battery may be further enhanced.

The polymer solid electrolyte provided in the present invention is used in a lithium secondary battery, and may be preferably used as a polymer solid electrolyte.

FIG. 1 is a sectional view illustrating a lithium secondary battery (10) of the present invention. When referring to FIG. 1, the lithium secondary battery (10) comprises a positive electrode (11), a negative electrode (15) and an electrolyte provided therebetween, and herein, a polymer solid electrolyte (13) is used as the electrolyte, and the polymer solid electrolyte provided above is used as the polymer solid electrolyte (13).

The polymer solid electrolyte (13) provided above exhibits high lithium ion conductivity while satisfying properties such as an electrochemically stable potential difference, low electrical conductivity and high temperature stability, and thereby is preferably used as a battery electrolyte to improve battery performance and thermal stability.

Moreover, in order to further increase lithium ion conductivity, the electrolyte (13) may further comprise materials used for this purpose.

When necessary, the polymer solid electrolyte (13) further comprises an inorganic solid electrolyte or an organic solid electrolyte. The inorganic solid electrolyte is a ceramic-based material, and crystalline or non-crystalline material may be used, and inorganic solid electrolytes such as thio-LISICON ($Li_{3.25}Ge_{0.25}P_{0.75}S_4$), $Li_2S$—$SiS_2$, $LiI$—$Li_2S$—$SiS_2$, $LiI$—$Li_2S$—$P_2S_5$, $LiI$—$Li_2S$—$P_2O_5$, $LiI$—$Li_3PO_4$—$P_2S_5$, $Li_2S$—$P_2S_5$, $Li_3PS_4$, $Li_2P_3S_{11}$, $Li_2O$—$B_2O_3$, $Li_2O$—$B_2O_3$—$P_2O_5$, $Li_2O$—$V_2O_5$—$SiO_2$, $Li_2O$—$B_2O_3$, $Li_3PO_4$, $Li_2O$—$Li_2WO_4$—$B_2O_3$, LiPON, LiBON, $Li_2O$—$SiO_2$, LiI, $Li_3N$, $Li_5La_3Ta_2O12$, $Li_7La_3Zr_2O_{12}$, $Li_6BaLa_2Ta_2O_{12}$, $Li_3PO_{(4-3/2w)}Nw$ (w is w<1) or $Li_{3.6}Si_{0.6}P_{0.4}O_4$ may be used.

Examples of the organic solid electrolyte may comprise those mixing a lithium salt to a polymer-based material such as polyethylene derivatives, polyethylene oxide derivatives, polypropylene oxide derivatives, phosphoric acid ester polymers, polyagitation lysine, polyester sulfide, polyvinyl alcohol or polyvinylidene fluoride. Herein, these may be used either alone or as a combination of at least one or more.

Specific methods of using as the polymer solid electrolyte (13) is not particularly limited in the present invention, and known methods may be selected or chosen by those skilled in the art.

A lithium secondary battery (10) capable of using the polymer solid electrolyte (13) as an electrolyte is not particularly limited in a positive electrode (11) or a negative electrode (15), and particularly, may be used in lithium-air batteries, lithium oxide batteries, lithium-sulfur batteries, lithium metal batteries, and all solid-state batteries operating at a high temperature.

As the positive electrode (11) of the lithium secondary battery (10), layer compounds such as lithium cobalt oxide ($LiCoO_2$) or lithium nickel oxide ($LiNiO_2$) or compounds substituted with one or more transition metals; lithium manganese oxides such as a chemical formula of $Li_{1+x}Mn_{2-x}O_4$ ($0 \le x \le 0.33$), $LiMnO_3$, $LiMn_2O_3$ or $LiMnO_2$; lithium copper oxide ($Li_2CuO_2$); vanadium oxides such as $LiV_3O_8$, $LiFe_3O_4$, $V_2O_5$ or $Cu_2V_2O_7$; Ni site-type lithium nickel oxides represented by a chemical formula of $LiNi_{1-x}M_xO_2$ (M=Co, Mn, Al, Cu, Fe, Mg, B or Ga; $0.01 \le x \le 0.3$); lithium manganese composite oxides represented by a chemical formula of $LiMn_{2-x}M_xO_2$ (M=Co, Ni, Fe, Cr, Zn or Ta; $0.01 \le x \le 0.1$) or $Li_2Mn_3MO_8$ (M=Fe, Co, Ni, Cu or Zn); spinel-structured lithium manganese composite oxides represented by $LiNi_xMn_{2-x}O_4$; $LiMn_2O_4$ in which some of Li in the chemical formula are substituted with alkaline earth metal ions; disulfide compounds; $Fe_2(MoO_4)_3$, chalcogenides such as $Cu_2Mo_6S_8$, FeS, CoS and MiS, oxides, sulfides or halides of scandium, ruthenium, titanium, vanadium, molybdenum, chromium, manganese, iron, cobalt, nickel, copper, zinc or the like may be used, and more specifically, $TiS_2$, $ZrS_2$, $RuO_2$, $Co_3O_4$, $Mo_6S_8$, $V_2O_5$ or the like may be used, however, the positive electrode is not limited thereto.

Such a positive electrode active material may be formed on a positive electrode current collector. The positive electrode current collector is not particularly limited as long as it has high conductivity without inducing chemical changes to the corresponding battery, and for example, stainless steel, aluminum, nickel, titanium, baked carbon, or aluminum or stainless steel of which surface is treated with carbon, nickel, titanium, silver or the like may be used. Herein, the positive electrode current collector may be used in various forms such as films, sheets, foil, nets, porous bodies, foams and non-woven fabrics with micro-unevenness formed on the surface so that adhesive strength with the positive electrode active material increases.

In addition, as the negative electrode (15), a negative electrode compound layer having a negative electrode active material is formed on a negative electrode current collector, or a negative electrode compound layer (lithium foil as one example) is used alone.

Herein, types of the negative electrode current collector or the negative electrode compound layer are not particularly limited in the present invention, and known materials may be used.

In addition, the negative electrode current collector is not particularly limited as long it has conductivity without inducing chemical changes to the corresponding battery, and for example, copper, stainless steel, aluminum, nickel, titanium, baked carbon, copper or stainless steel of which surface is treated with carbon, nickel, titanium, silver or the like, aluminum-cadmium alloys and the like may be used. In addition, like the positive electrode current collector, the negative electrode current collector may be used in various forms such as films, sheets, foil, nets, porous bodies, foams and non-woven fabrics with micro-unevenness formed on the surface.

In addition, the negative electrode active material may comprise one or more carbon-based materials selected from the group consisting of crystalline artificial graphite, crystalline natural graphite, amorphous hard carbon, low-crystalline soft carbon, carbon black, acetylene black, ketjen black, super-P, graphene and fibrous carbon, Si-based materials, metal composite oxides such as $LixFe_2O_3$ ($0 \le x \le 1$), $Li_xWO_2$ ($0 \le x \le 1$) or $Sn_xMe_{1-x}Me'_yO_z$ (Me:Mn, Fe, Pb, Ge; Me':Al, B, P, Si, elements of Groups 1, 2 and 3 in the periodic table, halogen; $0<x \le 1$; $1 \le y \le 3$; $1 \le z \le 8$); lithium metal; lithium alloys; silicon-based alloys; tin-based alloys; metal oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$ and $Bi_2O_5$; conductive polymers such as polyacetylene; Li—Co—Ni-based materials; titanium oxides; lithium titanium oxides, and the like, but is not limited thereto.

In addition thereto, as the negative electrode active material, metal composite oxides such as $SnxMe_{1-x}Me'_yO_z$ (Me: Mn, Fe, Pb, Ge; Me':Al, B, P, Si, elements of Groups 1, 2 and 3 in the periodic table, halogen; $0<x \le 1$; $1 \le y \le 3$; $1 \le z \le 8$); oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO2_2$, $Bi_2O_3$, $Bi_2O_4$ and $Bi_2O_5$, and the like, may be used, and carbon-based negative electrode active materials such as crystalline carbon, amorphous carbon or carbon composites may be used either alone or as a mixture of two or more types.

Herein, the electrode compound layer may further comprise a binder resin, a conductor, afiller, other additives and the like.

The binder resin is used for binding of the electrode active material and the conductor, and for binding on the current collector. Examples of such a binder resin may comprise polyvinylidene fluoride (PVDF), polyvinyl alcohol, carboxylmethylcellulose (CMC), starch, hydroxypropylcellulose, regenerated cellulose, polyvinyl pyrrolidone, tetrafluoroethylene, polyethylene, polypropylene, an ethylene-propylene-diene polymer (EPDM), a sulfonated-EPDM, styrene-butadiene rubber, fluorine rubber, various copolymers thereof, and the like.

The conductor is used for further enhancing conductivity of the electrode active material. Such a conductor is not particularly limited as long it has conductivity without inducing chemical changes to the corresponding battery, and examples thereof may comprise graphite such as natural graphite or artificial graphite; carbon black such as carbon black, acetylene black, ketjen black, channel black, furnace black, lamp black or thermal black; conductive fibers such as carbon fiber or metal fibers; fluorinated carbon, aluminum, metal powders such as nickel powder; conductive whiskers such as zinc oxide or potassium titanate; conductive metal oxides such as titanium oxide; polyphenylene derivatives, and the like.

The filler is optionally used as a component suppressing electrode expansion, and is not particularly limited as long as it is a fibrous material without inducing chemical changes to the corresponding battery. For example, olefin-based polymers such as polyethylene or polypropylene; fibrous materials such as glass fiber or carbon fiber are used.

The shape of the lithium secondary battery (10) described above is not particularly limited, and examples thereof may comprise a jelly-roll type, a stack type, a stack-folding type (comprising a stack-Z-folding type), or a lamination-stack type, and may preferably comprise a stack-folding type.

After preparing such an electrode assembly in which the negative electrode (15), the polymer solid electrolyte (13) and the positive electrode (11) are consecutively laminated, the result is placed in a battery case, and the result is sealed with a cap plate and a gasket and assembled to manufacture a lithium secondary battery.

Herein, depending on the used positive electrode/negative electrode materials, the lithium secondary battery (10) may be classified into various batteries such as a lithium-sulfur battery, a lithium-air battery, a lithium-oxide battery or a lithium all solid-state battery, and depending on the shape, may be classified into a cylinder type, a square-type, a coin-type, a pouch-type and the like, and depending on the size, may be classified into a bulk type and a thin-film type. Structures and manufacturing methods of these batteries are widely known in the art, and therefore, detailed descriptions will not be included.

The lithium secondary battery (10) according to the present invention may be used as a power supply of devices requiring high capacity and high rate properties. Specific examples of the device may comprise power tools operated through receiving electric power by a battery motor; electric vehicles including electric vehicles (EV), hybrid electric vehicles (HEV), plug-in hybrid electric vehicles (PHEV) and the like; electric two-wheeled vehicles including e-bikes and e-scooters; electric golf carts; systems for power storage and the like, but are not limited thereto.

Hereinafter, preferred examples will be provided in order to illuminate the present invention, however, the following examples are for illustrative purposes only, and it will be obvious to those skilled in the art that various changes and modifications may be made within the category and technological ideas of the present invention, and such changes and modifications also belong to the scope of the attached claims.

Example 1 to Example 10: Preparation of Polymer Solid Electrolyte Using Additive for Protecting Electrode A polymer solid electrolyte composition was prepared including a PEO polymer in the polymer solid electrolyte and by adding an additive for protecting an electrode as described in the following Table 1 thereto. Herein, the polymer solid electrolyte composition was prepared so that the content of the additive for protecting an electrode became 10% by weight with respect to a total weight of the polymer solid electrolyte composition.

As for the preparation method from Examples 1 to 10, one LiTFSI, a lithium salt, per ethylene oxide, a monomer, in PEO, the polymer solid electrolyte, was considered for the preparation. The temperature in the electrolyte liquid was based on 25° C., room temperature.

TABLE 1

| | Additive for Protecting Electrode |
|---|---|
| Example 1 | VC |
| Example 2 | SN |
| Example 3 | VEC |
| Example 4 | FEC |
| Example 5 | PBT |
| Example 6 | Chemical Formula 1 Compound (NSC-1) |
| Example 7 | Chemical Formula 2 Compound (NSC-2) |
| Example 8 | Chemical Formula 3 Compound (NSC-3) |
| Example 9 | Chemical Formula 4 Compound (NSC-4) |
| Example 10 | Chemical Formula 5 Compound (NSC-5) |
| Comparative Example1 | — |

Comparative Example 1: Preparation of Polymer Solid Electrolyte

A polymer solid electrolyte was prepared in the same manner as in Example 1 without using the additive for protecting an electrode.

Experimental Example 1: Evaluation on Degree of Positive Electrode Distribution of Additive for Protecting Electrode For the polymer solid electrolytes prepared in Examples 1 to 10, a degree of positive electrode distribution was evaluated using molecular dynamics for each type of the additives for protecting an electrode.

According to molecular dynamics, based on a phenomenon of electrolyte components such as an anion of a lithium salt, an electrolytic solution and an additive included in an electrolyte distributing on a positive electrode surface when charging a lithium secondary battery, a degree of distribution of the electrolyte components such as an anion of a lithium salt, an electrolytic solution and an additive on the positive electrode surface during charge may be calculated to relative compare and evaluate a degree of these materials favorably reaching the positive electrode surface.

FIGS. 2a to 2c are mimetic diagrams of a cell manufactured for evaluating a degree of electrolyte components reaching a positive electrode surface using molecular dynamics.

As illustrated in FIG. 2a, a cell (100) was formed by fixing an anion of a lithium salt ($PF_6^-$), an electrolytic solution (EC & EMC) and an additive so as not to escape through disposing two layers of graphite (G+, G−) as an electrode on both ends to mimic the electrode (Vatamanu et al, *JPCC*, 2012, 1114).

After that, as illustrated in FIG. 2*b*, the electrolyte was included in the cell (100), and under room temperature (25° C.) and a high temperature (60° C.), a molecular dynamics analysis was performed by setting potential ($E_{field}$), a voltage difference between the electrodes (G1, G2), at 0.6 V/nm.

As a force field for the molecular dynamics, a general AMBER force field (GAFF) [4] was used (Wang et al., *J. Comp. Chem.*, 2004, 1157)), and as for the lithium ions, optimized potentials for liquid simulations (OPLS) (Jorgensen et al., *JACS*, 1996, 11225) were used.

In addition, as illustrated in FIG. 2*c*, number density of the constituents was calculated based on the positive electrode (G+) surface, and using area and density of the peak closest to the electrode surface, the number of entities actually reaching the positive electrode surface was measured, and a percentage thereof in the whole was analyzed.

For the polymer solid electrolytes prepared in Examples 1 to 5, a molecular dynamics analysis was performed by, under room temperature (25° C.) and a high temperature (60° C.) in the cell (100) manufactured as in FIG. 2*a*, setting potential ($E_{field}$), a voltage difference between the electrodes (G+, G−), at 0.6 V/nm, and then a degree of distribution (Pi, first layer) of each of the additives for protecting an electrode on the positive electrode surface was measured.

FIG. 3 is a graph presenting, according to the polymer solid electrolytes each prepared in Examples 1 to 5, a degree of distribution ($Prob_{i, first\ layer}$) of the additive for protecting an electrode included in the positive electrode surface film when charging a lithium secondary battery in percentage (%).

When referring to FIG. 3, probability of distributing on the positive electrode surface turned out to be high in order of PBT<FEC<VEC<SN<VC among the additives for protecting an electrode used in Examples 1 to 5, and from this, it was identified that tendency of the additive for protecting an electrode reaching the positive electrode surface was high in this order. In addition, such a degree of distribution of the additives for protecting an electrode on the positive electrode surface tended to be similar at room temperature (25° C.) and a high temperature (60° C.) Ethylene carbonate (EC), gamma-butyrolactone (GBL) and cyclohexylbenzene (CHB) were measured as a reference.

FIG. 4 is a graph presenting, according to the polymer solid electrolytes each prepared in Examples 6 to 10, a degree of distribution ($Prob_{i, first\ layer}$) of the additive for protecting an electrode included in the positive electrode surface film when charging a lithium secondary battery.

When referring to FIG. 4, probability of distributing on the positive electrode surface turned out to be high in order of Chemical Formula 2 Compound (NSC-2)<Chemical Formula 3 Compound (NSC-3)<Chemical Formula 1 Compound (NSC-1)<Chemical Formula 4 Compound (NSC-4) <(CHB)<Chemical Formula 5 Compound (NSC-5)<(GBL) <(EC) among the additives for protecting an electrode used in Examples 6 to 10, and from this, it was identified that tendency of the additive for protecting an electrode reaching the positive electrode surface was high in this order. In addition, such a degree of distribution of the additives for protecting an electrode on the positive electrode surface tended to be similar at room temperature (25° C.) and a high temperature (60° C.) Ethylene carbonate (EC), gamma-butyrolactone (GBL) and cyclohexylbenzene (CHB) were measured as a reference.

Experimental Example 2: Measurement of HOMO Energy of Additive for Protecting Electrode For each of Chemical Formula 1 Compound to Chemical Formula 5 Compound, the additives used in Examples 6 to 10, a HOMO energy level was measured. The HOMO energy level was measured with a B3PW91/6-31+G* level in a Gaussian 09 program. Ethylene carbonate (EC), gamma-butyrolactone (GBL) and cyclohexylbenzene (CHB) were measured as a reference. EC, GBL and CHB are additives used in existing non-aqueous liquid electrolyte liquids.

FIG. 5 is a result measuring the HOMO energy level for the additive used in preparing each of the polymer solid electrolytes in Examples 6 to 10.

When referring to FIG. 5, it was seen that Chemical Formula 1 Compound to Chemical Formula 5 Compound (NSC-1 to NSC-5), the additives each used in Examples 6 to 10, had a higher HOMO energy level compared to EC and CHB, the additives used in existing non-aqueous liquid electrolyte liquids.

Hereinbefore, preferred embodiments of the present specification have been illustrated and described, however, the present specification is not limited to the specific embodiments described above, and various modified embodiments may be made by those skilled in the art without departing from the gist of the present invention that the claims claim, and such modified embodiments are not to be individually understood from technological ideas or perspectives of the present invention.

REFERENCE NUMERAL

10: Lithium Secondary Battery
11: Positive Electrode
13: Polymer Solid Electrolyte
15: Negative Electrode
100: Cell
G+: Graphite Positive Electrode
G−: Graphite Negative Electrode.

The invention claimed is:
1. A polymer solid electrolyte comprising:
a polymer for an electrolyte;
a lithium salt; and
an additive,
wherein the additive is an organic compound selected from the group consisting of a compound represented by the following Chemical Formula 1; a compound represented by the following Chemical Formula 2; a compound represented by the following Chemical Formula 3; a compound represented by the following Chemical Formula 4; a compound represented by the following Chemical Formula 5, and mixtures thereof:

Chemical Formula 1

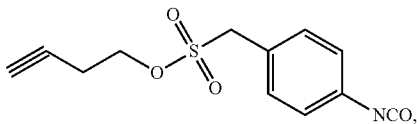

Chemical Formula 2

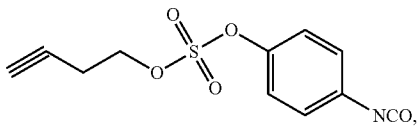

-continued

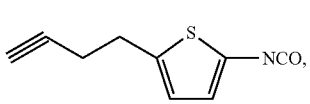

Chemical Formula 3

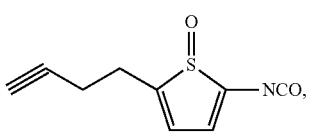

Chemical Formula 4

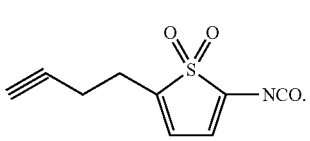

Chemical Formula 5

2. The polymer solid electrolyte of claim 1, wherein the additive is included in an amount of 0.1% by weight to 20% by weight based on a total weight of the polymer solid electrolyte.

3. The polymer solid electrolyte of claim 1, wherein the polymer for an electrolyte is one or more types selected from the group consisting of polyethylene oxide (PEO), polyethylene carbonate (PEC), polypropylene carbonate (PPC), poly(vinylidene fluoride) (PVDF), poly(ethylene glycol) (PEG), polyphenylene sulfide (PPS) and derivatives thereof.

4. The polymer solid electrolyte of claim 1, wherein the polymer for an electrolyte is included in an amount of 10% by weight to 30% by weight based on a total weight of the polymer solid electrolyte.

5. The polymer solid electrolyte of claim 1, wherein the lithium salt is one or more types selected from the group consisting of LiCl, LiBr, LiI, $LiClO_4$, $LiBF_4$, $LiB_{10}Cl_{10}$, $LiPF_6$, $LiAsF_6$, $LiSbF_6$, $LiAlCl_4$, LiSCN, $Li(FSO_2)_2N$ $LiCF_3CO_2$, $LiCH_3SO_3$, $LiCF_3SO_3$, $LiN(SO_2CF_3)_2$, LiTFSI, LiFSI, LiOH, $LiOHH_2O$, LiBOB, $LiN(SO_2C_2F_5)_2$, $LiC_4F_9SO_3$, $LiC(CF_3SO_2)_3$, $(CF_3SO_2)_2NLi$, $LiOH.H_2O$, $LiB(C_2O_4)_2$, chloroborane lithium, lower aliphatic carboxylic acid lithium, lithium tetraphenylborate and lithium imide.

6. The polymer solid electrolyte of claim 1, wherein the lithium salt is included in an amount of 10% by weight to 30% by weight based on a total weight of the polymer solid electrolyte.

7. The polymer solid electrolyte of claim 1, further comprising an organic solvent, wherein the organic solvent is one or more types selected from the group consisting of 4-acetylmorpholine, 2-methylpyridine-1-oxide, 2-pyrrolidone, 1-(2-hydroxyethyl)-2-pyrrolidone, propylene carbonate (PC), ethylene carbonate (EC), 2-oxepanone, butanone, 2-pentanone and methyl ethyl ketone (MEK).

8. A lithium secondary battery comprising the polymer solid electrolyte of claim 1.

* * * * *